(12) United States Patent
Odrich et al.

(10) Patent No.: US 9,463,114 B2
(45) Date of Patent: Oct. 11, 2016

(54) PUNCTAL PLUG WITH ACTIVE AGENT

(71) Applicant: MATI THERAPEUTICS INC., Austin, TX (US)

(72) Inventors: Steven A. Odrich, Bronx, NY (US); Liane C. Glazer, Chestnut Hill, MA (US)

(73) Assignee: Mati Therapeutics Inc., Austin, TX (US)

( * ) Notice: Subject to any disclaimer, the term of this patent is extended or adjusted under 35 U.S.C. 154(b) by 0 days.

(21) Appl. No.: 14/472,844

(22) Filed: Aug. 29, 2014

(65) Prior Publication Data

US 2015/0132358 A1 May 14, 2015

Related U.S. Application Data

(60) Continuation of application No. 13/533,676, filed on Jun. 26, 2012, now abandoned, which is a continuation of application No. 12/604,202, filed on Oct. 22, 2009, now abandoned, which is a division of application No. 10/825,047, filed on Apr. 15, 2004, now abandoned.

(51) Int. Cl.
*A61F 9/00* (2006.01)
*A61F 9/007* (2006.01)
*A61K 9/00* (2006.01)

(52) U.S. Cl.
CPC ......... *A61F 9/0017* (2013.01); *A61F 9/00772* (2013.01); *A61K 9/0051* (2013.01)

(58) Field of Classification Search
None
See application file for complete search history.

(56) References Cited

U.S. PATENT DOCUMENTS

| | | | |
|---|---|---|---|
| 3,828,777 A | 8/1974 | Ness | |
| 3,865,108 A | 2/1975 | Hartop | |
| 3,949,750 A | 4/1976 | Freeman | |
| 4,014,335 A | 3/1977 | Arnold | |
| 4,281,654 A | 8/1981 | Shell | |
| 4,660,546 A * | 4/1987 | Herrick | A61F 9/00772 128/898 |
| 4,886,488 A | 12/1989 | White | |
| 4,915,684 A | 4/1990 | MacKeen | |
| 4,959,048 A | 9/1990 | Seder | |
| 5,041,081 A | 8/1991 | Odrich | |
| 5,049,142 A | 9/1991 | Herrick | |
| 5,053,030 A | 10/1991 | Herrick | |
| 5,098,443 A | 3/1992 | Parel | |
| 5,116,371 A | 5/1992 | Christensen | |
| 5,128,058 A | 7/1992 | Ishii | |

(Continued)

FOREIGN PATENT DOCUMENTS

| | | |
|---|---|---|
| AU | 20023644336 | 7/2003 |
| EP | 0442745 A1 | 8/1991 |

(Continued)

OTHER PUBLICATIONS

Rathbone and Gurny, Ed. Controlled Release Veterinary Drug Delivery, 2000, p. 118.*

(Continued)

*Primary Examiner* — Nissa Westerberg
(74) *Attorney, Agent, or Firm* — Mati Therapeutics Inc.; Koren Anderson

(57) ABSTRACT

A method and apparatus for administering an active agent such as a medicine to a subject, uses an ocular implant such as a punctal plug, to which the active agent has been applied. The implant is installed at the eye of the subject for administering the active agent via tissues of the eye.

14 Claims, 2 Drawing Sheets

(56) References Cited

U.S. PATENT DOCUMENTS

| | | |
|---|---|---|
| 5,133,159 A | 7/1992 | Nelson |
| 5,163,959 A | 11/1992 | Herrick |
| 5,171,270 A | 12/1992 | Herrick |
| 5,283,063 A | 2/1994 | Freeman |
| 5,300,114 A | 4/1994 | Gwon |
| 5,318,513 A | 6/1994 | Leib |
| 5,322,691 A * | 6/1994 | Darougar .......... A61K 9/0051 424/427 |
| 5,334,137 A | 8/1994 | Freeman |
| 5,395,618 A | 3/1995 | Darougar |
| 5,417,651 A | 5/1995 | Guena |
| 5,423,777 A | 6/1995 | Tajiri |
| 5,443,505 A | 8/1995 | Wong |
| 5,466,233 A | 11/1995 | Weiner |
| 5,556,633 A | 9/1996 | Haddad |
| 5,707,643 A | 1/1998 | Ogura |
| 5,723,005 A | 3/1998 | Herrick |
| 5,741,292 A | 4/1998 | Mendius |
| 5,766,243 A | 6/1998 | Christensen |
| 5,770,589 A | 6/1998 | Billson |
| 5,773,019 A | 6/1998 | Ashton |
| 5,824,048 A | 10/1998 | Tuch |
| 5,824,073 A | 10/1998 | Peyman |
| 5,826,584 A | 10/1998 | Schmitt |
| 5,830,171 A | 11/1998 | Wallace |
| 5,840,054 A | 11/1998 | Hamano |
| 5,961,370 A | 10/1999 | Valle |
| 5,962,383 A | 10/1999 | Doyel |
| 5,993,407 A | 11/1999 | Moazed |
| 6,010,391 A | 1/2000 | Lewellen |
| 6,016,806 A | 1/2000 | Webb |
| 6,027,470 A | 2/2000 | Mendius |
| 6,041,785 A | 3/2000 | Webb |
| 6,082,362 A | 7/2000 | Webb |
| 6,095,901 A | 8/2000 | Robinson |
| 6,149,684 A | 11/2000 | Herrick |
| 6,196,993 B1 | 3/2001 | Cohan |
| 6,234,175 B1 | 5/2001 | Zhou |
| 6,238,363 B1 | 5/2001 | Kurihashi |
| 6,254,562 B1 | 7/2001 | Fouere |
| 6,264,971 B1 | 7/2001 | Darougar |
| 6,290,684 B1 | 9/2001 | Herrick |
| 6,306,114 B1 | 10/2001 | Freeman |
| 6,331,313 B1 | 12/2001 | Wong |
| 6,371,122 B1 | 4/2002 | Mandelkorn |
| 6,375,972 B1 | 4/2002 | Guo |
| 6,383,192 B1 | 5/2002 | Kurihashi |
| 6,428,502 B1 | 8/2002 | Lang |
| 6,441,047 B2 | 8/2002 | DeSantis |
| 6,455,062 B1 | 9/2002 | Olejnik |
| 6,605,108 B2 | 8/2003 | Mendius |
| 6,629,533 B1 | 10/2003 | Webb |
| 6,706,275 B1 | 3/2004 | Camp |
| 6,729,939 B2 | 5/2004 | Wrue |
| 6,756,049 B2 | 6/2004 | Brubaker |
| 6,780,164 B2 | 8/2004 | Bergheim |
| 6,840,931 B2 | 1/2005 | Peterson |
| 6,846,318 B2 | 1/2005 | Camp |
| 6,866,563 B2 | 3/2005 | Green |
| 6,964,781 B2 | 11/2005 | Brubaker |
| 6,982,090 B2 | 1/2006 | Gillespie |
| 6,991,808 B2 | 1/2006 | Brubaker |
| 6,994,684 B2 | 2/2006 | Murray |
| 7,001,615 B1 * | 2/2006 | Singh ............ A61K 9/0043 424/486 |
| 7,017,580 B2 | 3/2006 | Prescott |
| 7,117,870 B2 | 10/2006 | Prescott |
| 7,135,009 B2 | 11/2006 | Tu |
| 7,204,253 B2 | 4/2007 | Mendius |
| 7,204,995 B2 | 4/2007 | El-Sherif |
| 2002/0032400 A1 | 3/2002 | Moazed |
| 2002/0055701 A1 | 5/2002 | Fischell |
| 2002/0103255 A1 * | 8/2002 | Hellberg ............ A61K 31/215 514/530 |
| 2002/0151960 A1 | 10/2002 | Mendius |
| 2002/0193441 A1 | 12/2002 | Robertson |
| 2002/0198453 A1 | 12/2002 | Herrick |
| 2003/0130612 A1 | 7/2003 | Moazed |
| 2004/0102729 A1 | 5/2004 | Haffner |
| 2004/0121014 A1 | 6/2004 | Guo |
| 2004/0127843 A1 | 7/2004 | Tu |
| 2004/0137068 A1 | 7/2004 | Bhushan |
| 2004/0141151 A1 | 7/2004 | Gillespie |
| 2004/0147870 A1 | 7/2004 | Burns |
| 2004/0170685 A1 | 9/2004 | Carpenter |
| 2004/0175410 A1 | 9/2004 | Ashton |
| 2004/0210182 A1 | 10/2004 | Fouere |
| 2004/0249333 A1 | 12/2004 | Bergheim |
| 2004/0265356 A1 | 12/2004 | Mosack |
| 2005/0048121 A1 | 3/2005 | East |
| 2005/0095269 A1 | 5/2005 | Ainpour |
| 2005/0129731 A1 | 6/2005 | Horres |
| 2005/0197614 A1 | 9/2005 | Pritchard |
| 2005/0220882 A1 | 10/2005 | Pritchard |
| 2005/0232972 A1 | 10/2005 | Odrich |
| 2005/0244469 A1 | 11/2005 | Whitcup |
| 2005/0266047 A1 | 12/2005 | Tu |
| 2005/0271704 A1 | 12/2005 | Tu |
| 2005/0283109 A1 | 12/2005 | Peyman |
| 2006/0013835 A1 | 1/2006 | Anderson |
| 2006/0020248 A1 | 1/2006 | Prescott |
| 2006/0020253 A1 | 1/2006 | Prescott |
| 2006/0074370 A1 | 4/2006 | Zhou |
| 2006/0100700 A1 | 5/2006 | Bernard |
| 2006/0106352 A1 | 5/2006 | Kurihashi |
| 2006/0122553 A1 | 6/2006 | Hanna |
| 2007/0083146 A1 | 4/2007 | Murray |
| 2007/0123924 A1 | 5/2007 | Becker |
| 2007/0132125 A1 | 6/2007 | Rastogi |
| 2007/0135914 A1 | 6/2007 | Herrick |
| 2007/0243230 A1 | 10/2007 | de Juan |
| 2007/0269487 A1 | 11/2007 | de Juan |
| 2007/0298075 A1 | 12/2007 | Borgia |
| 2007/0299515 A1 | 12/2007 | Herrick |
| 2007/0299516 A1 | 12/2007 | Cui |
| 2008/0038317 A1 | 2/2008 | Chang |
| 2008/0045878 A1 | 2/2008 | Bergheim |
| 2008/0045911 A1 | 2/2008 | Borgia |
| 2009/0092654 A1 | 4/2009 | de Juan |
| 2009/0104243 A1 | 4/2009 | Utkhede |
| 2009/0104248 A1 | 4/2009 | Rapacki |
| 2009/0105749 A1 | 4/2009 | de Juan |
| 2009/0118702 A1 | 5/2009 | Lazar |
| 2010/0040670 A1 | 2/2010 | Odrich |

FOREIGN PATENT DOCUMENTS

| | | |
|---|---|---|
| EP | 0621022 A1 | 10/1994 |
| JP | 10033584 | 2/1998 |
| JP | 2004202276 A | 7/2004 |
| JP | 2005000628 A | 1/2005 |
| JP | 2005058622 A | 3/2005 |
| JP | 2005110765 A | 4/2005 |
| JP | 2005110930 A | 4/2005 |
| JP | 2005312835 A | 11/2005 |
| JP | 2005319190 A | 11/2005 |
| JP | 2005328922 A | 12/2005 |
| JP | 2007195819 A | 8/2007 |
| WO | WO-9833461 | 8/1998 |
| WO | WO-9842282 | 10/1998 |
| WO | WO-9937260 | 7/1999 |
| WO | WO-9944553 | 9/1999 |
| WO | WO-9964089 | 12/1999 |
| WO | WO-9965544 | 12/1999 |
| WO | WO-0003705 | 1/2000 |
| WO | WO-0027321 | 5/2000 |
| WO | WO-0062760 | 10/2000 |
| WO | WO-0211783 | 2/2002 |
| WO | WO-02058667 | 8/2002 |
| WO | WO-02083198 | 10/2002 |
| WO | WO-03017897 | 3/2003 |
| WO | WO-03022242 | 3/2003 |
| WO | WO-03057101 | 7/2003 |
| WO | WO-2004004614 | 1/2004 |

(56) References Cited

FOREIGN PATENT DOCUMENTS

| WO | WO-2004024043 | 3/2004 |
|---|---|---|
| WO | WO-2004105658 | 12/2004 |
| WO | WO-2004112639 | 12/2004 |
| WO | WO-2005000154 | 1/2005 |
| WO | WO-2005086694 | 9/2005 |
| WO | WO-2006014434 | 2/2006 |
| WO | WO-2006031658 | 3/2006 |
| WO | WO-2006044669 | 4/2006 |
| WO | WO-2006057859 | 6/2006 |
| WO | WO-2006096586 | 9/2006 |
| WO | WO-2007008262 | 1/2007 |
| WO | WO-2007115259 | 10/2007 |
| WO | WO-2007115261 | 10/2007 |
| WO | WO-2007149771 | 12/2007 |
| WO | WO-2007149832 | 12/2007 |
| WO | WO-2008056060 | 5/2008 |
| WO | WO-2008094989 | 8/2008 |
| WO | WO-2009035562 | 3/2009 |

OTHER PUBLICATIONS

Carter et al. Ophthalmic Plastic and Reconstructive Surgery 4(4), p. 231-233, 1988.*
"U.S. Appl. No. 10/825,047, Response filed Apr. 22, 2009 to Non Final Office Action mailed Oct. 22, 2008", 17 pgs.
"U.S. Appl. No. 10/825,047,Final Office Action mailed Jun. 9, 2009", 14 pgs.
"U.S. Appl. No. 10/825,047,Non-Final Office Action mailed Oct. 22, 2008", 13 pgs.
"U.S. Appl. No. 10/825,047,Response filed Aug. 18, 2008 to Restriction Requirement mailed Jul. 17, 2008", 10 pgs.
"U.S. Appl. No. 10/825,047,Response filed Oct. 22, 2009 to Final Office Action mailed Jun. 9, 2009", 20 pgs.
"U.S. Appl. No. 10/825,047,Restriction Requirement mailed Jul. 17, 2008", 6 pgs.
"U.S. Appl. No. 11/571,147,Restriction Requirement mailed Jun. 26, 2009", 5 pgs.
"U.S. Appl. No. 11/695,537, Notice mailed Nov. 28, 2008 Regarding a Noncompliant or Nonresponsive Amendment filed on Nov. 3, 2008", 3 pgs.
"U.S. Appl. No. 11/695,537, Response filed Nov. 3, 2008 to Restriction Requirement mailed Oct. 3, 2008", 15 pgs.
"U.S. Appl. No. 11/695,537, Response filed Dec. 17, 2008 to Office Communication mailed Nov. 28, 2008", 8 pgs.
"U.S. Appl. No. 11/695,537, Restriction Requirement mailed Oct. 3, 2008", 10 pgs.
"U.S. Appl. No. 11/695,545, Preliminary Amendment and Response filed Nov. 6, 2008 to Restriction Requirement mailed Oct. 6, 2008", 14 pgs.
"U.S. Appl. No. 11/695,545, Restriction Requirement mailed Oct. 6, 2008", 10 pgs.
"U.S. Appl. No. 12/604,202, Preliminary Amendment filed Nov. 30, 2009", 6 pgs.
Dejuan, Jr E, "Expandable Nasolacrimal Drainage System Implants", U.S. Appl. No. 60/970,696, filed Sep. 7, 2007, 82 pgs.
Dejuan, Jr E, "Manufacture of Expandable Nasolacrimal Drainage System Implants", U.S. Appl. No. 60/970,720, filed Sep. 7, 2007, 57 pgs.
Dejuan, Jr E, "Multiple Drug Delivery Systems and Combinations of Drugs With Punctal Implants", U.S. Appl. No. 60/970,820, filed Sep. 7, 2007, 67 pgs.
"European Application Serial No. 05768122.3, Supplementary European Search Report mailed Mar. 31, 2009", 3 pgs.
"European Application Serial No. 05768122.3,Office Action mailed Apr. 17, 2009", 6 pgs.
Fukano, Y., et al., "Influence of Benzalkonium Chloride on the Penetration of Latanoprost into Rabbit Aqueous Humor After Ocular Instillations", AAPS Journal, vol. 8(S2), (2006),1pg.
Goskonda, V. R., et al., "Permeability of Chemical Delivery Systems Across Rabbit Corneal (SIRC) Cell Line and Isolated Corneas: A Comparative Study", Pharmaceutical Development and Technology, 5(3), (Abstract Only), (Jul. 2000), 1 pg.
"Impregnate—Definition by Dictionary.com", Accessed Apr. 6, 2011.
"International Application Serial No. PCT/US07/65792, International Search Report mailed Nov. 20, 2008", 2 pgs.
"International Application Serial No. PCT/US07/65792, International Written Opinion mailed Nov. 20, 2008", 5 pgs.
"International Application Serial No. PCT/US2007/065789, International Search Report mailed Aug. 13, 2008", 3 pgs.
"International Application Serial No. PCT/US2007/065789, Written Opinion mailed Aug. 13, 2008", 5 pgs.
"International Application Serial No. PCT/US2008/010479, International Search Report mailed Dec. 15, 2008", 6 pgs.
"International Application Serial No. PCT/US2008/010479, Written Opinion mailed Dec. 15, 2008", 7 pgs.
"International Application Serial No. PCT/US2008/010487, International Search Report mailed May 25, 2009", 5 pgs.
"International Application Serial No. PCT/US2008/010487, Written Opinion mailed May 25, 2009", 8 pgs.
Kaur, I. P., et al., "Chapter 25—Ocular Penetration Enhancers", In: Enhancement in Drug Delivery, (2007), 527-548.
Lazar, E, "Treatment Medium Delivery Device and Methods for Delivery of Such Treatment Mediums to the Eye Using Such a Delivery Device", U.S. Appl. No. 11/571,147, filed Dec. 21, 2006, 32 pgs.
Nakajima, M. et al., "Assessment of Drug Concentrations in Tears in Therapeutic Drug Monitoring: I. Determination of Valproic Acid in Tears by Gas Chromatography/Mass Spectrometry With EC/NCI Mode", Therapeutic Drug Monitoring, 22, (2000), 716-722.
"Oasis Product Catalog", (Apr. 2009), 7 pgs.
"Production Information for EaglePlug(r) TearFlow tm", (c) 2009 EagleVision, Inc., Memphis, TN, (2009), 1 pg.
"Production Information for the Micro Flow™ Punctal Occluder", Odyssey Medical, 1 pg.
Reich, C, et al., "Manufacture of Drug Cores for Sustained Release of Therapeutic Agents", U.S. Appl. No. 60/970,699, filed Sep. 7, 2007, 66 pgs.
Reich, Jr, Carl J.,et al "Nasolacriminal Drainage System Implants for Drug Delivery", U.S. Appl. No. 60/970,709, filed Sep. 7, 2007, 103 pgs.

* cited by examiner

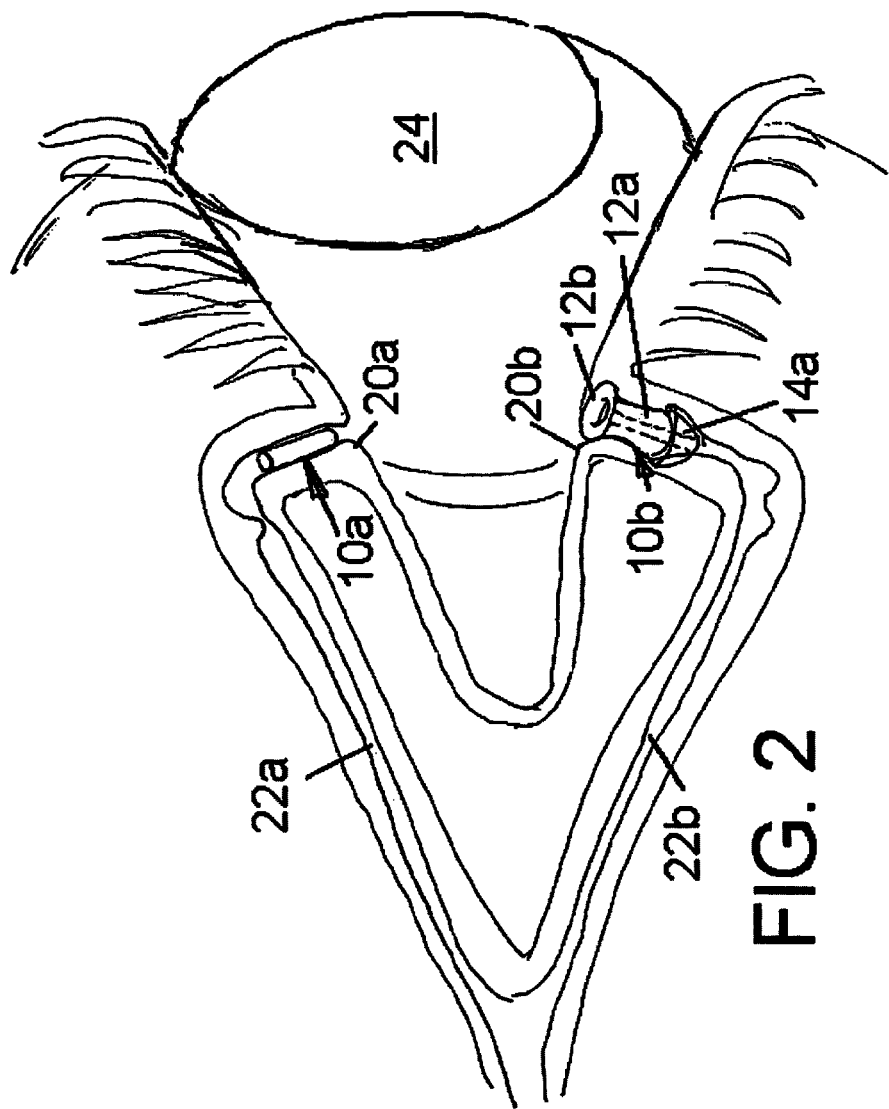

PUNCTAL PLUG WITH ACTIVE AGENT

This application is a continuation application of U.S. Ser. No. 13/533,676, Filed 26 Jun. 2012; which is a continuation application of U.S. Ser. No. 12/604,202, filed Oct. 22, 2009; which is a divisional application of U.S. Ser. No. 10/825,047, filed Apr. 15, 2004; the contents of each application are incorporated herein by reference in their entireties.

FIELD AND BACKGROUND OF THE INVENTION

Punctal plugs are known which are made in suitable dimensions and of suitable materials to be removably inserted into the upper and/or lower punctal apertures or punctum of the eye, to block the opening and the canaliculus communicating therewith, to prevent drainage of lacrimal fluid (tears). Such plugs are known to be made of suitable materials, such as polymers, for example polytetrafluoroethylene (known by the trademark TEFLON), or hydroxyethylmethacrylate (HEMA), hydrophilic polymer, methyl methacrylate, or silicon, or even of stainless steel or other inert metal material.

It is also known to apply an active agent such as nicotine or a birth control drug, to the inner surface of a patch which can be worn against the skin of a subject for transdermally administering the active agent to the subject.

SUMMARY OF THE INVENTION

It is an object of the present invention to provide a method and an apparatus for administering an active agent to a subject by applying the active agent to at least one surface of an ocular implant such as a punctal plug, and installing the implant, e.g. inserting the punctal plug into a punctal aperture of the subject.

If the active agent or drug is meant for treating the tissues at the walls of the canaliculus, for example, the drug is applied only to inner surfaces of the plug that are adapted to be in contact with or near the tissues of the canaliculus. The presence of tears is highly advantageous as a natural vehicle or carrier for the agent.

If the active agent or drug is meant for treating the eye itself, the drug is applied only to outer surfaces of the implant or plug that are adapted to be outside the canaliculus. Here the presence of previously secreted tears or a tear pool is again advantageous as a natural vehicle or carrier for the agent.

Any or all surfaces of the implant may carry the active agent there the desire is simply to have the agent enter the subjects blood stream via the tissues in and around the eye.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 2 is a perspective view of the area around the eye with other embodiments of the invention.

DESCRIPTION OF THE PREFERRED EMBODIMENT

Figure 1:
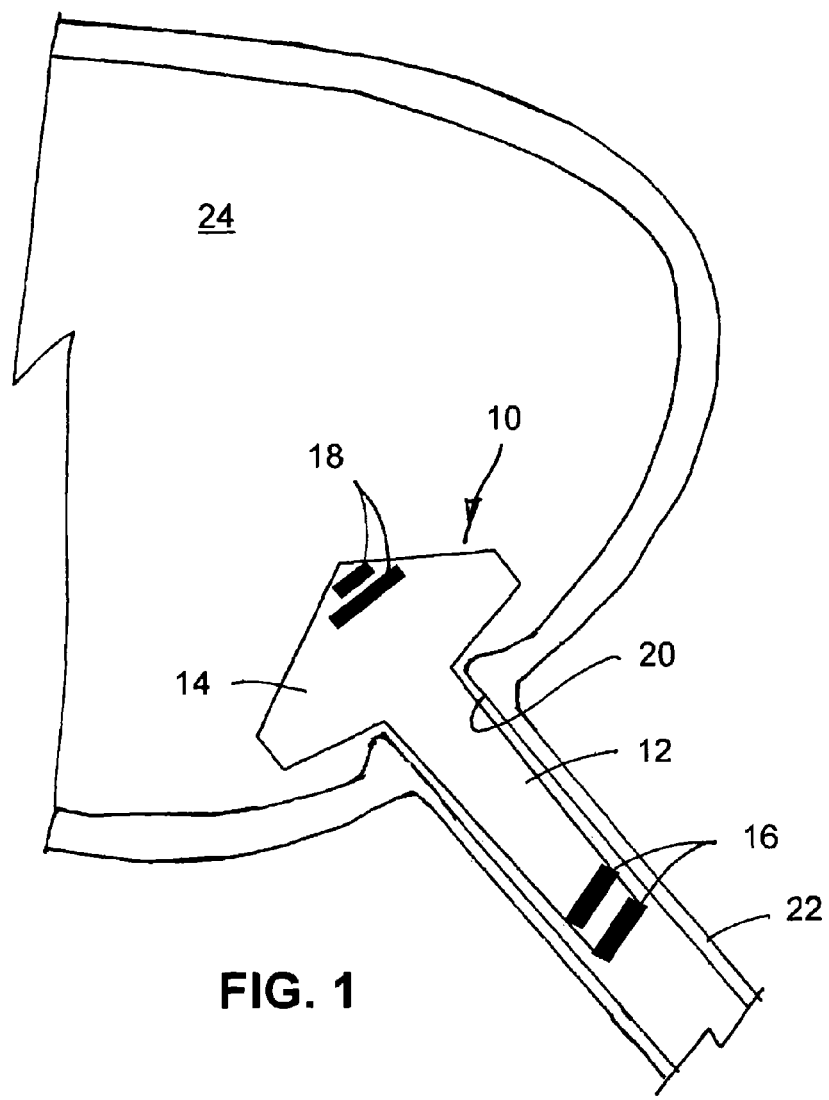
FIG. 1 is a schematic perspective view of an ocular implant in the form of a punctal plug according to the present invention.

Referring now to the drawing, FIG. 1 shows a punctal plug generally designated 10, having a stem 12 for insertion into the punctal aperture 20 of an eye 24, and along the canaliculus 22 communicating with the aperture.

Plug 10 has a large stopper structure 14 connected to the outer end of stem 12 for seating against the aperture 20 and sealing the canaliculus 22 against the flow of tears onto the surface of the eye or eyeball 24.

FIG. 2, where the same of similar numerals are used to designate functionally similar parts, illustrates an eye 24 communicating with upper and lower canaliculi 22a and 22b, each with their our implant 10a and 10b. Implant 10a is a substantially cylindrical and solid collagen plug that has been inserted into the upper punctum or tear duct 20a, to block the flow of tears while lower implant 10b is hollow like a straw for the passage of tears. Implant 10b includes a tapered shaft or stem 12a with a flared open end 12b immobilized at the lower punctum 20b. A mushroom shaped inner stopper 14a is formed at the opposite end of shaft 12a for further setting the location of the implant in the tear duct.

One of the embodiments illustrated in FIG. 2, e.g. the upper implant, may include a hollow core of the plug and another, e.g. the lower one, may include a hollow core filled with medication.

The active agent, e.g. a medicine or medication is applied, e.g. in one or more bands of polymer material 16 at the inner end of the stem, or at 18 on the outer end of the stopper 14 in the embodiment of FIG. 1, or over some or all of the surfaces of the implants of FIG. 2, or otherwise. Polymer that is absorbent to the agent is preferable so that sufficient agent is present and available for discharge into the surrounding tissues. A porous or absorbent material can alternatively be used to make up the entire plug or implant which can be saturated with the active agent.

The hollow implant 10b of FIG. 2 is also particularly useful in that the active agent can be applied to, or is otherwise available at the inner surface or interior of the implant, and is uniquely structured to pass tears and thus administer the active agent to the tear stream in a fashion that is controlled by the flow of tears which thus act as the carrier for the agent. Unlike the usual tear stopping punctal plug, the hollow implant of the present invention provides a very different drug administering method, scheme and structure.

Non-limiting examples of the active agents or medications which are appropriate for use with the invention include, for example only: topical prostaglandin derivatives such as latanoprost, travaprost and bimataprost used for the topical treatment of glaucoma. Also a treatment for corneal infections is appropriate using ciprofloxacin, moxifloxacin or gatifloxacin. Systemic medications useful for this invention are those used for hypertension such as atenolol, nifedipine or hydrochlorothiazide. Any other chronic disease requiring chronic medication could be used.

The treatment of allergic conjunctivitis and rhinitis are also good applications for the invention, e.g. using antihistamine and anti-allergy medication such as olopatadine and cromalyn sodium in or on the implant.

The advantage is that there would be no need for chronic pill-taking or drop taking. A once-per 3-6 month visit to the eye doctor would be all that is needed. Also the issue of non-compliance, a major impediment to successful treatment, would by avoided by the invention.

This list of active agents is not comprehensive in that many other agents can be used with the present invention. For example, a treatment for dry eye by topical cyclosporin is particularly interesting for administration by the present invention, but many other active agents can also be administered using the method and apparatus of the invention.

The invention is meant to embody all implants or devices which are implanted into the eye-lid canalicular puncta of the naso-lacrimal system with the goal of delivering drug to the eye or to the body.

The implant is inserted into either the inferior (lower) or superior (upper) punctum or possibly both. The apparatus is constructed so as to have a drug attached to one or both sides of the implant and an occlusive plug of some inert biocompatible material.

Depending on the desired therapy, the implant could be oriented in the punctal canal to deliver the drug either to the tear lake and thus the eye, or to the nasolacrimal system and thus the body's systemic circulation. The drawings illustrate only three embodiments of the punctal plug or implant delivery system of the invention.

While a specific embodiment of the invention has been shown and described in detail to illustrate the application of the principles of the invention, it will be understood that the invention may be embodied otherwise without departing from such principles.

What is claimed is:

1. A method for administering an active agent to a subject using a punctal plug, the method comprising:
   inserting the punctal plug into a punctal aperture of the subject, wherein the composition of the punctal plug comprises:
   a) an active agent selected from the group consisting of topical prostaglandin; latanoprost; travoprost; bimatoprost; a medication for treatment of a corneal infection; ciprofloxacin; moxifloxacin; gatifloxacin; a systemic medication; a medication for treating hypertension; atenolol; nifedipine; hydrochlorothiazide; and a medication for treating allergic conjunctivitis, and
   b) a porous or absorbent material, and
wherein the shape of the punctal plug consists of a constant diameter cylinder configured to be inserted into a canalicular puncta of the subject.

2. The punctal plug of claim 1, wherein the topical prostaglandin is latanoprost.

3. The punctal plug of claim 1, wherein the topical prostaglandin is travoprost.

4. The punctal plug of claim 1, wherein the topical prostaglandin is bimatoprost.

5. The punctal plug of claim 1, wherein the active agent is moxifloxacin.

6. The punctal plug of claim 1, wherein the active agent is a medication for the topical treatment of glaucoma or corneal infection.

7. The punctal plug of claim 1, wherein the plug body comprises hydrophilic polymers.

8. A method for administering an active agent to a subject using a punctal plug, the method comprising:
   inserting the punctal plug into a punctal aperture of the subject, wherein the composition of the punctal plug comprises:
   a) an active agent selected from the group consisting of topical prostaglandin; latanoprost; travoprost; bimatoprost; a medication for treatment of a corneal infection; ciprofloxacin; moxifloxacin; gatifloxacin; a systemic medication; a medication for treating hypertension; atenolol; nifedipine; hydrochlorothiazide; and a medication for treating allergic conjunctivitis, and
   b) a hydrophilic polymer, and
wherein the shape of the punctal plug consists of a constant diameter cylinder configured to be inserted into a canalicular puncta of the subject.

9. The punctal plug of claim 8, wherein the topical prostaglandin is latanoprost.

10. The punctal plug of claim 8, wherein the topical prostaglandin is travoprost.

11. The punctal plug of claim 8, wherein the topical prostaglandin is bimatoprost.

12. The punctal plug of claim 8, wherein the active agent is moxifloxacin.

13. The punctal plug of claim 8, wherein the active agent is a medication for the topical treatment of glaucoma or corneal infection.

14. A method for administering an active agent to a subject using a punctal plug, the method comprising:
   inserting the punctal plug into a punctal aperture of the subject, wherein the composition of the punctal plug comprises:
   a) an active agent wherein the active agent is selected from the group comprising: travoprost; moxifloxacin; and a medication for treating allergic conjunctivitis, and
   b) a hydrophilic polymer,
wherein the shape of the punctal plug consists of a constant diameter cylinder configured to be inserted into a canalicular puncta of the subject.

* * * * *